(12) United States Patent
DeWalt

(10) Patent No.: US 9,592,406 B2
(45) Date of Patent: Mar. 14, 2017

(54) EQUIPMENT FOR PRODUCING ULTRAVIOLET LIGHT

(71) Applicant: Douglas Gary DeWalt, Ottawa Hills, OH (US)

(72) Inventor: Douglas Gary DeWalt, Ottawa Hills, OH (US)

( * ) Notice: Subject to any disclaimer, the term of this patent is extended or adjusted under 35 U.S.C. 154(b) by 0 days.

(21) Appl. No.: 14/754,896

(22) Filed: Jun. 30, 2015

(65) Prior Publication Data

US 2017/0001031 A1    Jan. 5, 2017

(51) Int. Cl.
| | | |
|---|---|---|
| *A61N 5/00* | (2006.01) | |
| *A61N 5/06* | (2006.01) | |
| *H05B 37/02* | (2006.01) | |
| *G21K 5/00* | (2006.01) | |
| *A61L 2/00* | (2006.01) | |

(52) U.S. Cl.
CPC .......... *A61N 5/0614* (2013.01); *A61L 2/0047* (2013.01); *G21K 5/00* (2013.01); *H05B 37/0281* (2013.01); *A61N 2005/0615* (2013.01)

(58) Field of Classification Search
USPC ................................ 250/493.1, 503.1, 504 R
See application file for complete search history.

(56) References Cited

U.S. PATENT DOCUMENTS 7,834,335 B2 * 11/2010 Harmon .................... A61L 2/10
                                                           250/455.11
8,312,641 B2 * 11/2012 Li ............................. F26B 3/28
                                                           118/642

* cited by examiner

*Primary Examiner* — Nicole Ippolito
*Assistant Examiner* — Hanway Chang
(74) *Attorney, Agent, or Firm* — Fay Sharpe LLP

(57) ABSTRACT

Equipment including a lamp for producing UV light in the range 300-314 nm wavelength having spectral power in the range 302-307 nm wavelength across a 5 nm bandwidth of 40% of overall spectral power and spectral power in the range 307-312 nm of 40% of overall spectral power with a reflector of 90% reflectance in the range 300-314 nm wavelength. A key operated arming switch is series connected to a timer switch.

12 Claims, 6 Drawing Sheets

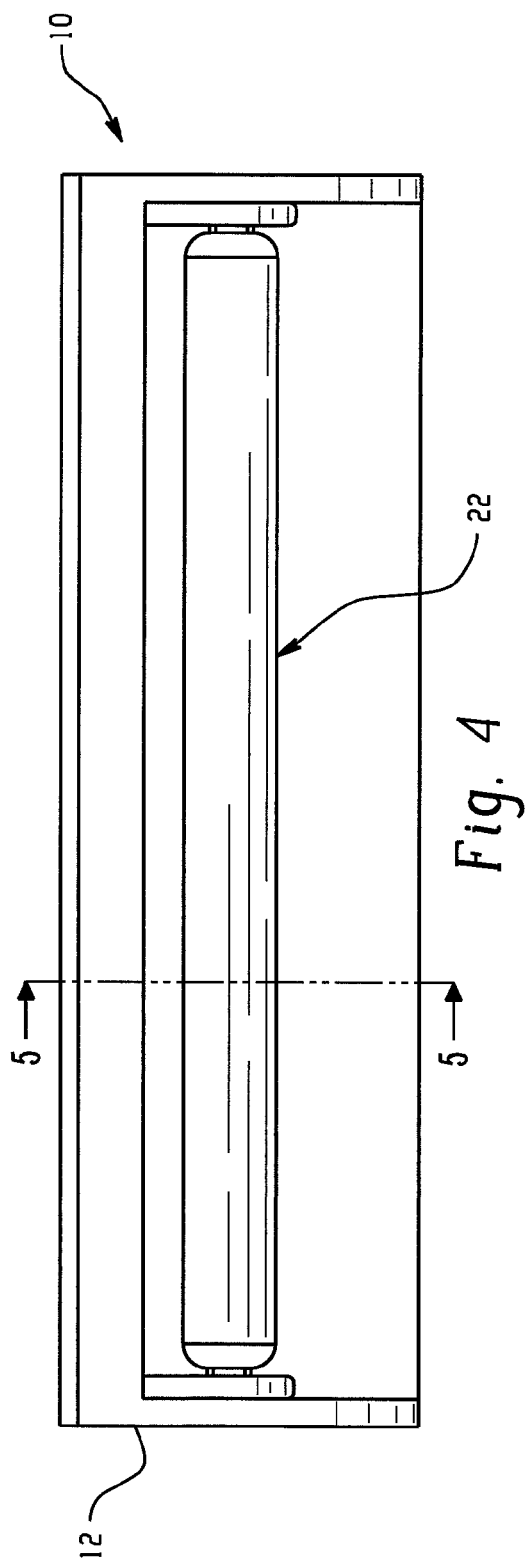
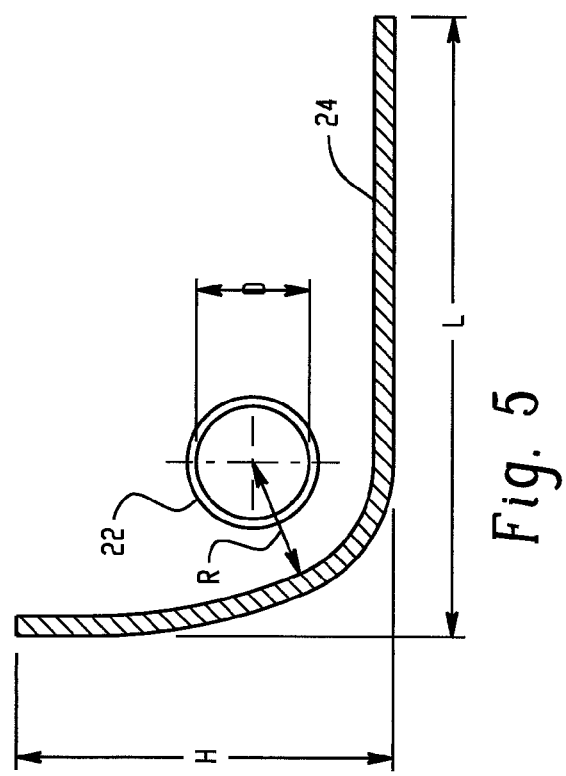
Fig. 4
Fig. 5 ically available prior art UV lamp;
EQUIPMENT FOR PRODUCING ULTRAVIOLET LIGHT

BACKGROUND

Ultraviolet light has been found useful for irradiating living tissue such as human skin for purposes such as tanning and for destroying microorganisms for sterilization purposes. Ultraviolet (UV) irradiation, which is outside the visible spectrum and which has a wavelength in the range of 100-400 nanometers (nm) has been informally classified as UV-A, having a wavelength in the range of 315-400 nm, UV-B, having a wavelength in the range of 280-315 nm and UV-C, having a wavelength in the range of 100-280 nm. Heretofore, UV-B has been that which is employed widely for irradiating human skin for tanning or cosmetic purposes and for use as a germicidal.

The more common sources of UV-B radiation have heretofore been lamps having a tubular configuration using an enclosed low pressure mercury arc source enclosed within a quartz or fused silica glass tube with the interior surface of the tube coated with a phosphor material for fluorescent conversion of emitted radiation.

In using UV radiation for tanning purposes UV-B and UV-C below 300 nm have been found to present a danger of over irradiation producing burning of the living tissue; therefore, lamps intended for such purposes are generally restricted below 10% UV-B to UVA irradiation. UV-A emanating from solar radiation is known to have deeper dermal penetration that destroys DNA and vitamin D3 in cellular tissue, and is thus to be avoided for such usage.

FIGS. 1 and 2 show typical examples of the spectral power distribution of presently commercially available UV-B lamps for which it is noted that a large majority of the power is less than 40% in any narrow frequency range which results in limited effectiveness of the lamps for the aforesaid purposes.

Therefore, it has been desired to provide equipment for generating UV-B irradiation that has the optimal benefit for use with living cellular tissue and as a germicidal without increasing the risks of damage to the living tissue.

SUMMARY

The present disclosure describes equipment for providing ultraviolet light radiation in a limited frequency band in which the spectral power of at least 40% of the total irradiance of the lamp is concentrated. This concentration of the ultraviolet light particularly in the UV-B range has proven to be efficacious for tanning purposes, therapeutic treatment of psoriasis, and as a germicidal. The equipment includes an ultraviolet radiation emitting lamp where the radiation is provided by electromagnetic wave generator emitting UV-B radiation in the range of 300-314 nm wavelength with a spectral power in the range 302-307 nm wavelength measured across a 5 nm bandwidth of at least 40% of the overall spectral power of the emitted irradiance of the lamp and the spectral in the range of 307-312 nm is of at least 40% of the overall spectral power. The wave generator is connected to the source of electrical power through a timed switch and includes a series connected switch operated by the user. In the present practice, the user operated switch includes a key operated cylinder lock and the key is removable only when the user operated switch is in the position opening the circuit to de-energize the wave generating lamp. In one embodiment, the wave generating lamp is of the mercury vapor type and, in another embodiment, a light emitting diode (LED array) is employed. The equipment includes a reflector formed of material having a high reflectance of 90% in the range of 300-314 nm wavelength.

The present disclosure thus describes equipment for empowering ultraviolet light in a "mid-band" wavelength band of about 5 nm in which the spectral power is in excess 40% of the total emitted irradiance of the lamp which has been found to have therapeutic value in treating psoriasis and as a germicidal.

BRIEF DESCRIPTION OF THE DRAWINGS

FIG. 4 is a plan view of the equipment assembly of the present disclosure;

FIG. 5 is a cross section taken along section indicating lines 5-5 of FIG. 4;

DETAILED DESCRIPTION

Figure 1:
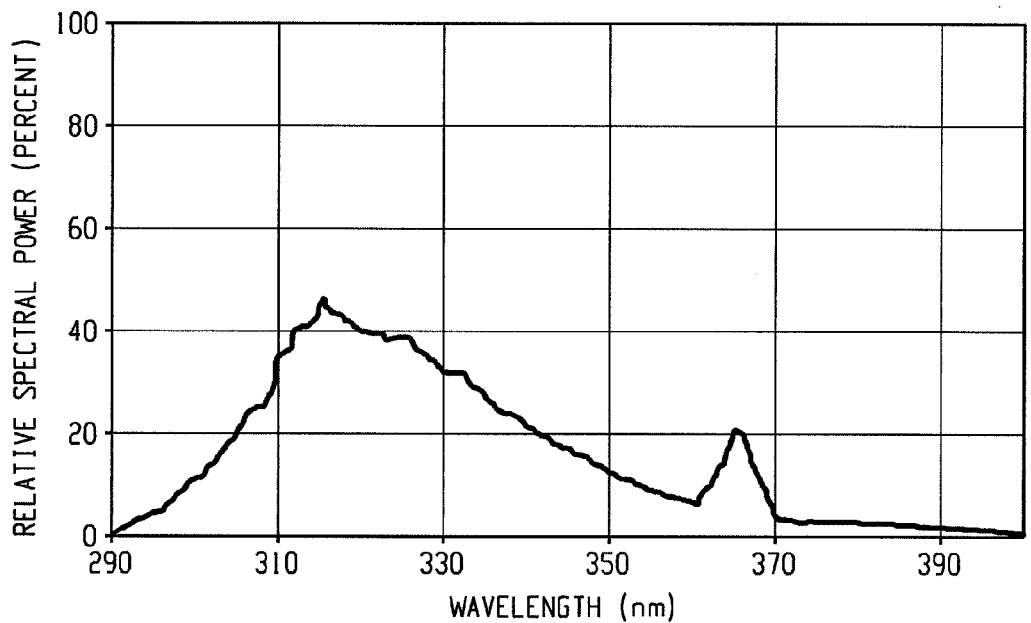
FIG. 1 is a plot of spectral power as a function of wavelength for a commercially available prior art UV lamp.
Figure 2:
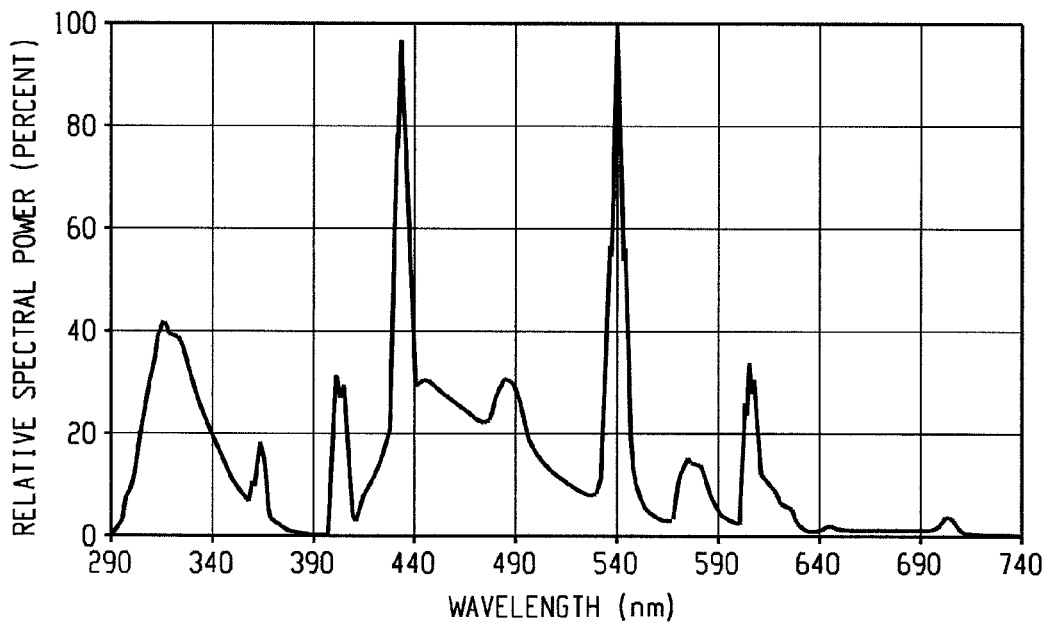
FIG. 2 is a plot similar to FIG. 1 of spectral power as a function of wavelength for another commercially available prior art UV lamp.
Figure 3:
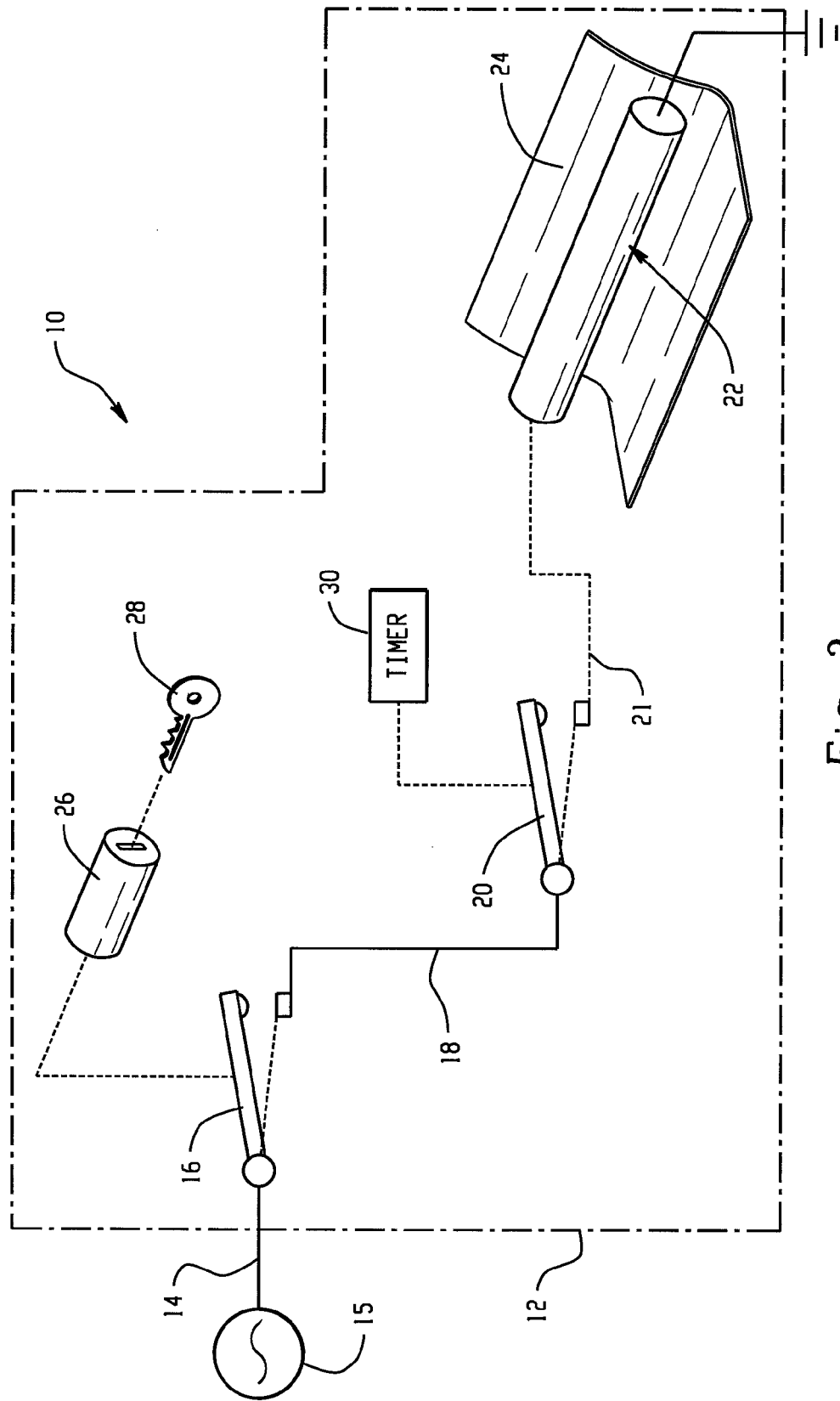
FIG. 3 is an electro-mechanical schematic of the equipment of the present disclosure.

Referring to FIGS. 3-5, the equipment is indicated generally at 10 and is provided in housing 12 and has electrical power 16 connected through lead 14 to a common terminal of a switch 16 which is series connected through lead 18 to timer activated switch 20 which has its closed terminal connected via lead 21 to a power inlet terminal of an ultra violet lamp indicated generally at 22. The lamp includes a reflector 24 which will be described hereinafter in greater detail. The switch 16 is activated by a cylinder lock mechanism 26, which, upon insertion of a key 28 and rotation by the user, effects closure of switch 16 and arming of the timer activated switch 20. A timer 30 may be set by the user for controlling switch 20 and providing predetermined desired time of operation of the lamp 22. In the present practice, the cylinder lock 26 for activating switch 16 is of the type that the key cannot be removed when the lock is rotated to a position closing switch 16. Therefore, the user must rotate the key and cylinder lock to the "off" position to open the switch 16 before the key may be removed from the cylinder lock 26.

In the present practice, the UV lamp 22 is one of a mercury vapor lamp and a light emitting diode array and is typically housed in a UVC-blocking quartz or fused silica glass tube. In the present practice, the lamp 22 has 40% of its overall spectral power of emitted irradiance within the restricted band of 300-314 nm wavelength. In the present practice, it has been found satisfactory to have the interior of the tube coated with a phosphor having a chemical composition of one of (Y,Gd) Mg $B_6O_{10}$:Ce, Pr and Mg Sr $Al_{10}O_{17}$:Ce.

In the present practice, the UV lamp of 14.7 watts provides 1350 µW/cm²/nm upon exposure for 5 minutes at a distance of 6 inches (15.2 cm) from the subject or target; provides 135 µW/cm²/nm upon exposure for 5 minutes at a distance of 12 inches (30.4 cm); and, also provides 135 µW/cm²/nm upon exposure for 40 minutes at a distance of 20-24 inches (50.8 to 60.9 cm).

Referring to FIG. 5, the arrangement of the lamp and reflector is illustrated in detail in which the reflector 24 has in cross section a generally curved right angle configuration. In the present practice, it has been found satisfactory to form the reflector material having a thickness of 0.10 mm of polished non-anodized aluminum. However, any material having a surface reflectance of at least 90% of irradiation in the 300-314 nm range could be employed. In the version illustrated in FIG. 5, for a lamp of 14.7 watts, the dimension "H" is 30 mm; the dimension "L" is 60 mm; and, the internal diameter of the tube is 0.8 inches (20.3 mm). The center of the tube having the aforesaid configuration is, in the present practice, satisfactorily located at the dimension "R" of 35 mm from the surface of the reflector. The reflector may be formed of other materials as a substrate with a coating of aluminum or aluminum tape.

Figure 6:
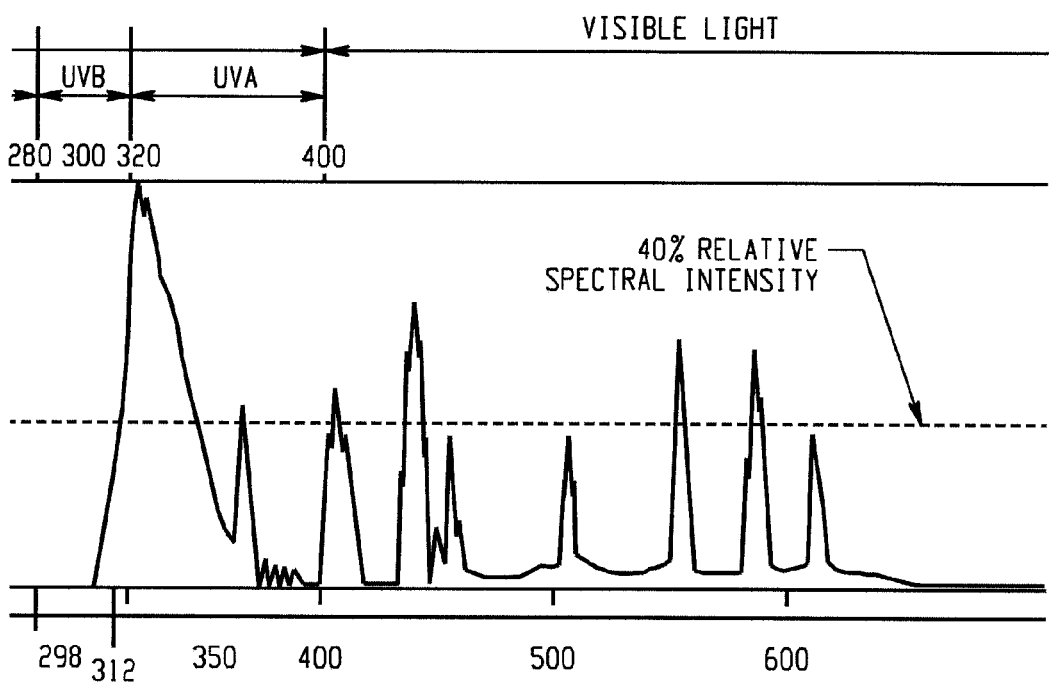
FIG. 6 is a plot of spectral power as a function of wavelength of a typical lamp for the equipment of the present disclosure.
Figure 7:
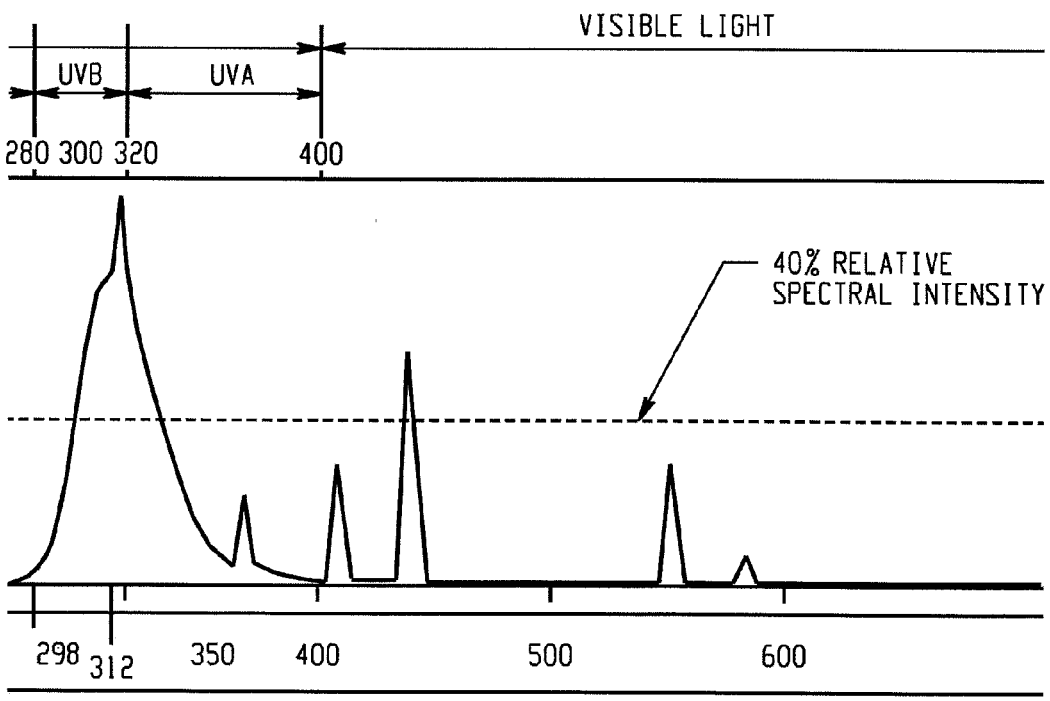
FIG. 7 is a plot similar to FIG. 6 of another typical lamp for the equipment of the present disclosure.

Referring to FIGS. 6 and 7, typical graphs of wavelength versus relative spectral intensity for typical examples of lamps, in accordance with the present disclosure, are illustrated. It will be seen from FIGS. 6 and 7 that, typically, a substantial portion of the irradiance of the lamp occurs in the 300-314 nm wavelength band.

Figure 8:
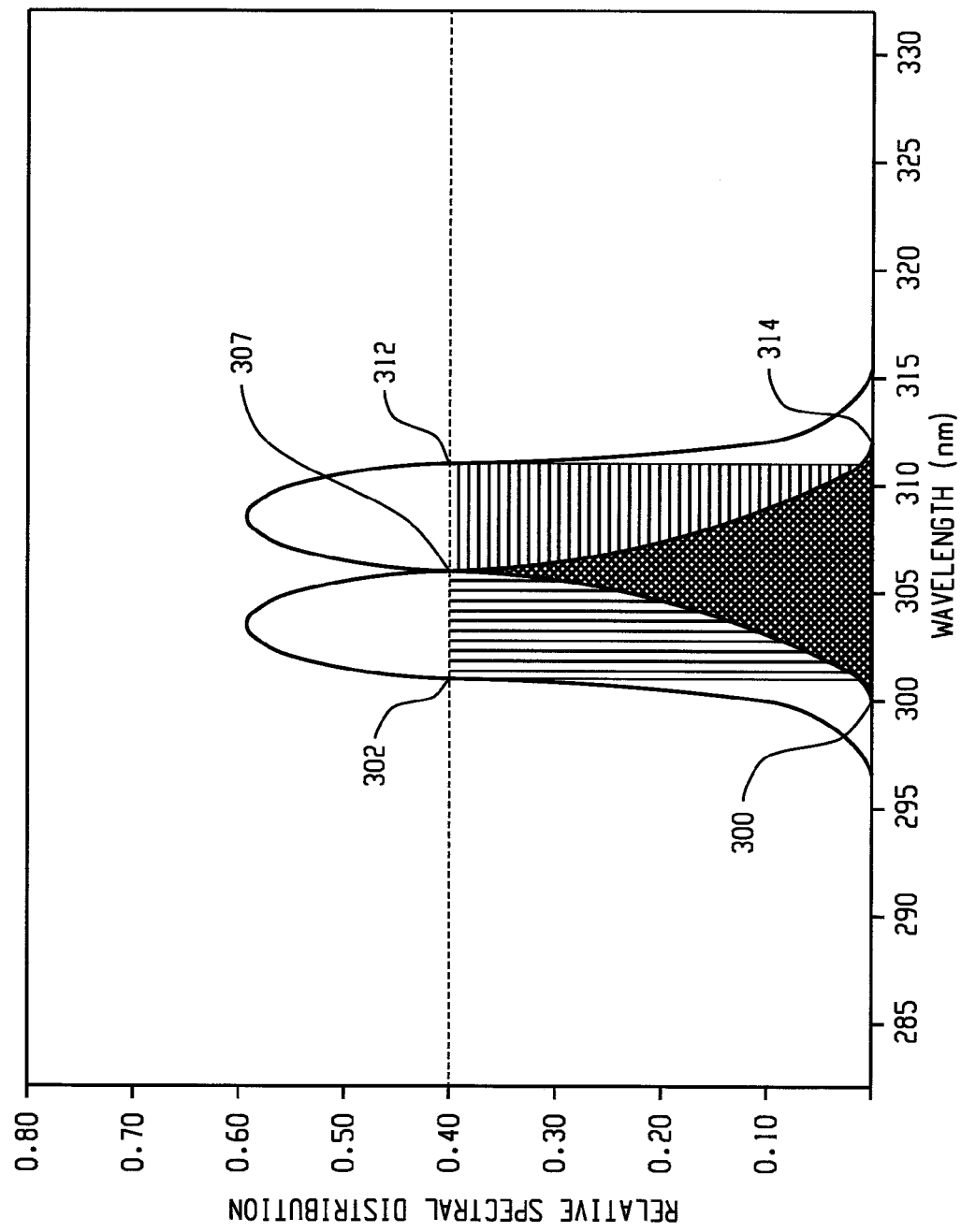
FIG. 8 is a plot of the minimum requirements spectral power as a function of wavelength distributions as measureable in practice (sensors, optical filtration) for the equipment of the present disclosure; and, FIG. 9 is a plot of spectral power as a function of wavelength measured for a lamp of equipment of the present disclosure.

Referring to FIG. 8, similar graphs are illustrated showing theoretically minimum spectral distribution examples of the lamp in accordance with the present disclosure having at least 40% spectral distribution within the 300-314 nm wavelength region. The left peaked plot illustrates required spectral power distribution of 40% in the range 302-307 nm wavelength and the right peaked plot illustrates required spectral power distribution of 40% in the range 307-312 nm wavelength.

Figure 9:
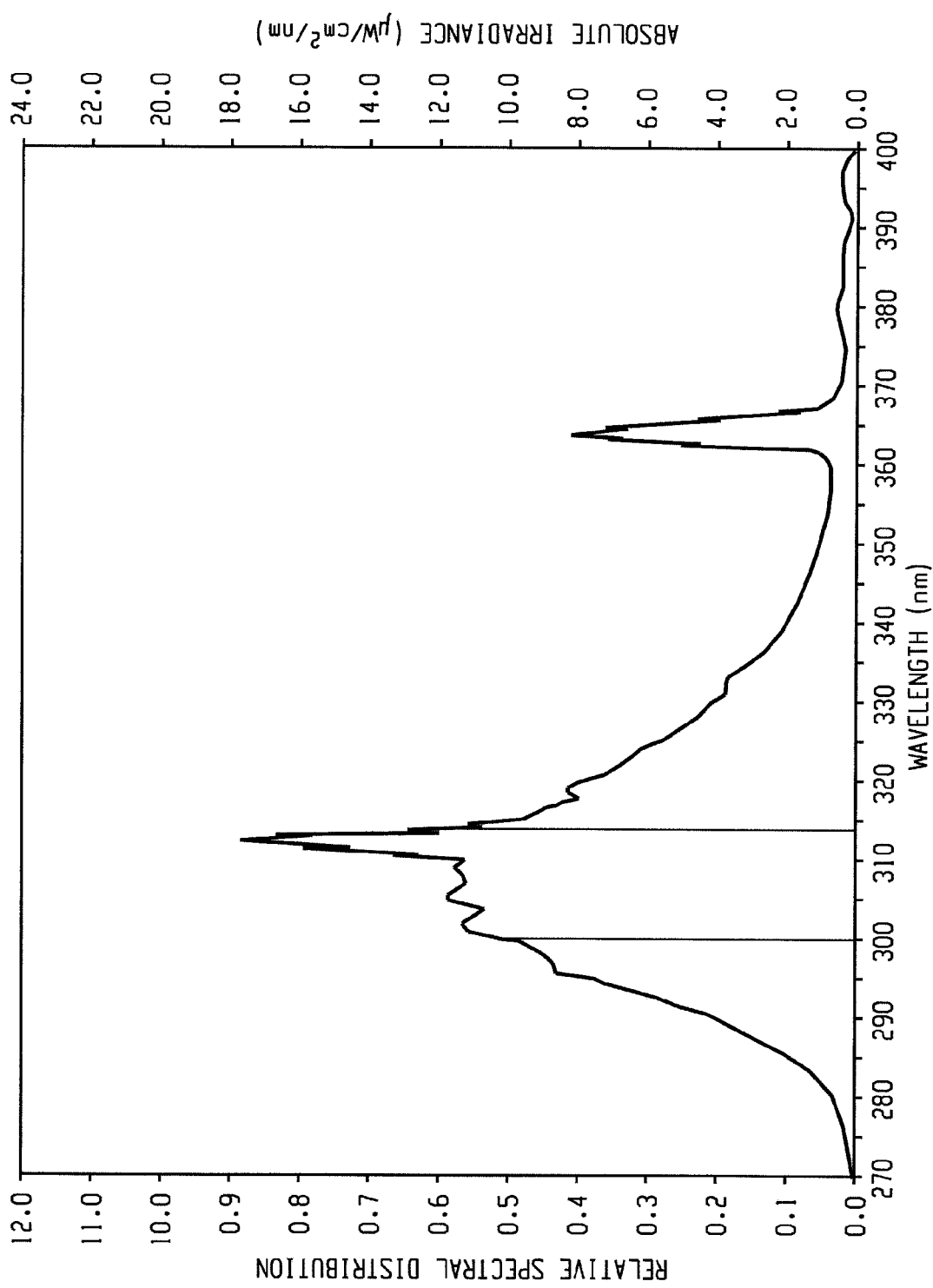

Referring to FIG. 9, another actual example of the measured spectral distribution of the lamp, in accordance with the present disclosure, is illustrated wherein the distribution is above the 40% level for the entire restricted band but includes a peak or spike above 310 nm wavelength.

The present disclosure thus describes equipment for providing irradiance of ultra violet light in a restricted band in the region of 300-314 nm wavelength in which 40% of the relative spectral power of the irradiance is within the restricted band, thus, providing increased therapeutic and germicidal properties. The equipment includes a reflector formed of relatively thin aluminum sheet in a curved or angular configuration which in a polished non-anodized configuration provides at least 90% reflectance of the radiation in the restricted band.

The equipment includes a time switch series connected with a manually activated switch in which the user inserts the key in a cylinder lock and rotates the cylinder lock to arm the timer switch. The cylinder lock is arranged such that the user must turn the key to the "off" position before removing the key.

The exemplary embodiment has been described with reference to the preferred embodiments. Obviously, modifications and alterations will occur to others upon reading and understanding the preceding detailed description. It is intended that the exemplary versions described herein be construed as including all such modifications and alterations insofar, as they come within the scope of the appended claims or the equivalents thereof.

The invention claimed is:

1. Equipment for producing UV-B ultraviolet (UV) light for in vivo therapeutic purposes, comprising:
   (a) an electromagnetic wave generator lamp operable upon connection to a source of electrical power to emit ultra violet (UV) radiation in the range of 300-314 nanometers (nm) wavelength having spectral power in the range of 302-307 (nm) wavelength being measured across a five (5) nm bandwidth of wavelength of at least 40% of the overall spectral power of the emitted irradiance of the lamp and the spectral power in the range of 307-312 nm of at least 40% of the overall spectral power;
   (b) a timed switch electrically series connected to the said generator; and, operative to de-energize the wave generator after a predetermined interval;
   (c) a user operated switch series connected with the timed switch; and,
   (d) a reflector providing 90% reflectance in the range 300-314 nm wavelength disposed proximate the wave generator for reflecting the UV radiation.

2. The equipment of claim 1, wherein the user operated switch includes a key operated cylinder lock, wherein the key is removable only with the user operated switch in an open circuit position.

3. The equipment of claim 1, wherein the generator includes an ultra violet emitting tube lamp.

4. The equipment of claim 1, wherein the timed switch includes a user selected period of time-out.

5. The equipment of claim 1, wherein the generator includes one of a mercury vapor lamp and a light emitting diode (LED ARRAY).

6. The equipment of claim 1, wherein the remaining UV spectral power other than the forty percent is within the range of 290-400 nm.

7. The system of claim 1, wherein the lamp comprises a tube coated with a phosphor having a chemical composition of one of (Y,Gd) Mg B6O10:Ce, Pr and Mg Sr Al10O17:Ce.

8. The system of claim 1, wherein the reflector is formed of a non-anodized polished aluminum material.

9. The system of claim 8, wherein the reflector has a generally curved right angle configuration in cross section.

10. In a method of irradiating UV-B ultra violet light onto a user for therapeutic purposes, the improvement comprising:
   (a) providing an ultra violet (UV) lamp emitting radiation having its spectral power of 300-314 nm wavelength and the spectral power in the range of 302-307 nm of at least 40% of the overall UV irradiance of the lamp; and, the spectral power in the range of 307-312 nm of at least 40% of the overall UV irradiance of the lamp;
   (b) disposing the lamp at least 152 mm from the tissue to be treated and energizing the lamp for a predetermined time interval; and, upon expiration of the said time interval, automatically de-energizing the lamp;
   (c) connecting a user actuated switch in series with the lamp;
   (d) providing a reflector having a reflectance of 90% in the range of 300-314 nm wavelength; and,
   (e) reflecting the emitted radiation onto the user.

11. The method of claim 10, wherein the connecting a user actuated switch includes connecting a key operated switch permitting removal of the key only in an open circuit position.

12. The method of claim 10, wherein providing a UV lamp includes providing a UV lamp emitting 1350 $\mu W/cm^2/nm$ upon exposure for 5 minutes at a distance of 15.2 cm, 135 $\mu W/cm^2/nm$ upon exposure for 5 minutes at a distance of 30.4 cm, and 135 $\mu W/cm^2/nm$ upon exposure for 40 minutes at a distance of 50.8 to 60.9 cm.

\* \* \* \* \*